(12) United States Patent
Sullivan

(10) Patent No.: US 12,065,670 B2
(45) Date of Patent: Aug. 20, 2024

(54) *DROSOPHILA* STOCK MAINTENANCE

(71) Applicant: THE REGENTS OF THE UNIVERSITY OF CALIFORNIA, Oakland, CA (US)

(72) Inventor: William T. Sullivan, Oakland, CA (US)

(73) Assignee: The Regents of the University of California, Oakland, CA (US)

(*) Notice: Subject to any disclaimer, the term of this patent is extended or adjusted under 35 U.S.C. 154(b) by 0 days.

(21) Appl. No.: 18/484,560

(22) Filed: Oct. 11, 2023

(65) Prior Publication Data

US 2024/0034989 A1 Feb. 1, 2024

Related U.S. Application Data

(62) Division of application No. 17/585,338, filed on Jan. 26, 2022, now Pat. No. 11,814,646, which is a division of application No. 16/159,596, filed on Oct. 12, 2018, now abandoned.

(60) Provisional application No. 62/577,457, filed on Oct. 26, 2017.

(51) Int. Cl.
| | |
|---|---|
| *A01K 67/033* | (2006.01) |
| *C12M 1/00* | (2006.01) |
| *C12M 1/12* | (2006.01) |
| *C12M 3/00* | (2006.01) |
| *C12N 5/07* | (2010.01) |

(52) U.S. Cl.
CPC .......... *C12N 5/0601* (2013.01); *A01K 67/033* (2013.01); *C12M 23/06* (2013.01); *C12M 23/22* (2013.01); *C12M 23/34* (2013.01); *C12M 23/44* (2013.01); *C12M 23/46* (2013.01); *C12M 25/10* (2013.01)

(58) Field of Classification Search
None
See application file for complete search history.

(56) References Cited

U.S. PATENT DOCUMENTS

| | | |
|---|---|---|
| 3,595,086 A | 7/1971 | Bonnet et al. |
| 3,687,110 A | 8/1972 | Braunhut |
| | | (Continued) |

OTHER PUBLICATIONS

Teshler et al., "A Novel Device for the Collection, Storage, Transport, and Delivery of Beneficial Insects, and its Application to *Ophraella communa* (Coleoptera: Chrysomelidae)", Biocontrol Science and Technology (Jun. 2004), vol. 14, No. 4, 347-357.

*Primary Examiner* — Holly Kipouros
(74) *Attorney, Agent, or Firm* — Carter, DeLuca & Farrell LLP

(57) ABSTRACT

An insect culture maintenance system includes a sequence of open-ended cylindrical tubes joined pairwise alternately at their tops and bottoms using multiple dual-cap connectors. Each dual-capped connector has a channel from an inside of a first cap to an inside of a second cap. In use, connectors that cap the bottoms of the tubes are filled with insect food media, while connectors that cap the tops of the tubes are open. As a result of this design, adults pass from one tube to the next through the top dual-cap connectors, while larvae pass from one tube to the next through the bottom dual-cap connectors, resulting in propagation of subsequent generations of insects through the sequence of tubes.

14 Claims, 4 Drawing Sheets

(56) References Cited

U.S. PATENT DOCUMENTS

| | | | |
|---|---|---|---|
| 3,789,799 A * | 2/1974 | Orfei | A01K 67/033 |
| | | | 119/6.5 |
| 3,874,335 A | 4/1975 | Galasso | |
| 4,106,438 A | 8/1978 | Nelson | |
| 4,328,636 A | 5/1982 | Johnson | |
| 4,676,256 A | 6/1987 | Golden | |
| 4,799,599 A | 1/1989 | Herrmann | |
| 7,935,523 B2 | 5/2011 | Atehortua et al. | |
| 8,753,325 B2 | 6/2014 | Lev et al. | |
| 10,051,845 B1 * | 8/2018 | Massaro | A01K 29/005 |
| 11,814,646 B2 | 11/2023 | Sullivan | |
| 2009/0030662 A1 | 1/2009 | Guirguis | |
| 2009/0123908 A1 | 5/2009 | Petersson | |
| 2009/0130740 A1 | 5/2009 | Ophardt | |
| 2017/0219462 A1 | 8/2017 | Whelan | |
| 2018/0332842 A1 | 11/2018 | Tsao | |

* cited by examiner

*Fig. 1*
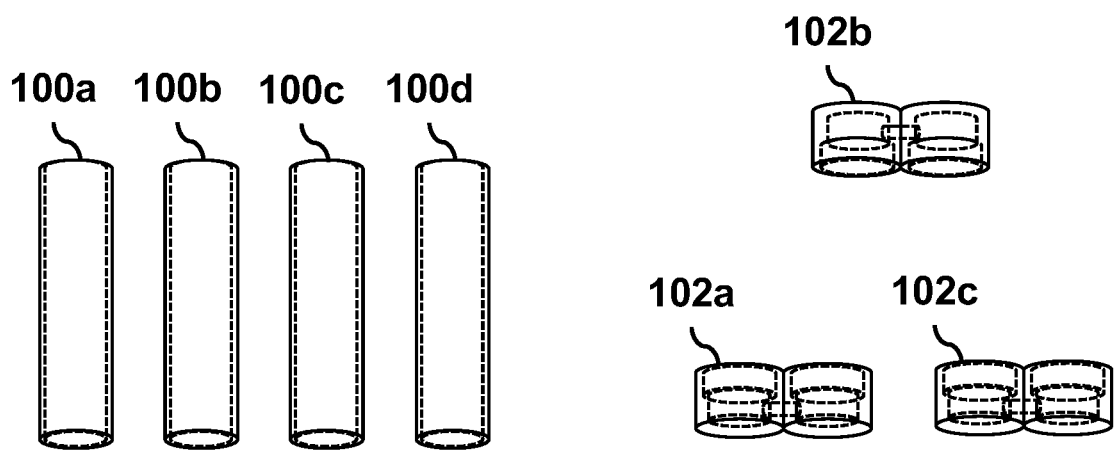
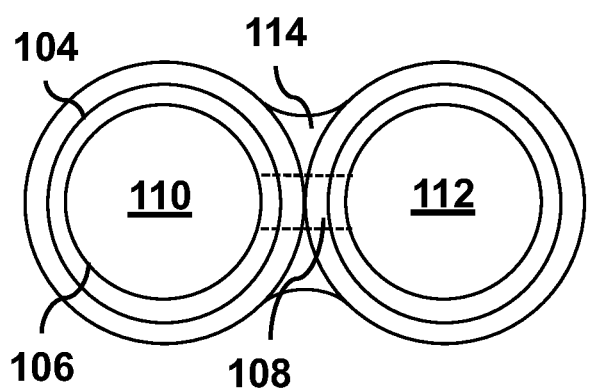
*Fig. 2A*
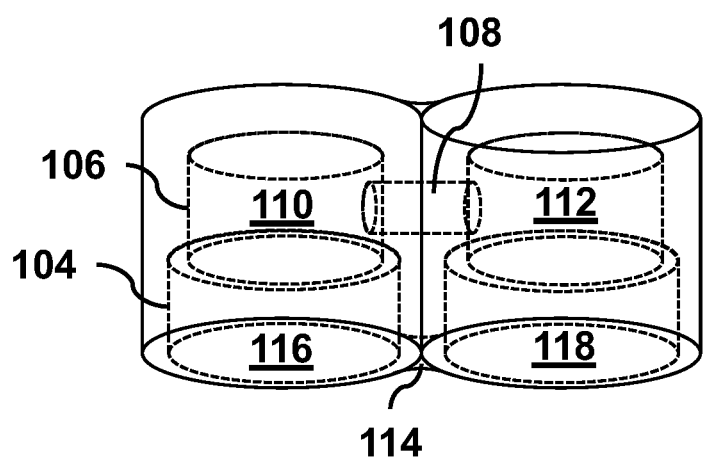
*Fig. 2B*

Fig. 6

600 Connect tubes in sequence using the food media filled dual caps on the bottoms of the tubes and empty dual caps on the tops; insert adult flies in first tube, where they will lay eggs; cap the tops of the first and last tubes.

602 First generation larvae propagate in food media through opening in first dual cap from the bottom of the first tube to the bottom of the second tube; first generation larvae mature into first generation adults in the second tube.

604 First generation adults propagate through opening in the second dual cap from the top of the second tube to the top of the third tube; first generation adults lay eggs in food media in bottom of third tube.

606 Second generation larvae propagate in food media through opening in second dual cap from the bottom of the third tube to the bottom of the fourth tube; second generation larvae mature into second generation adults in the fourth tube.

Fig. 7

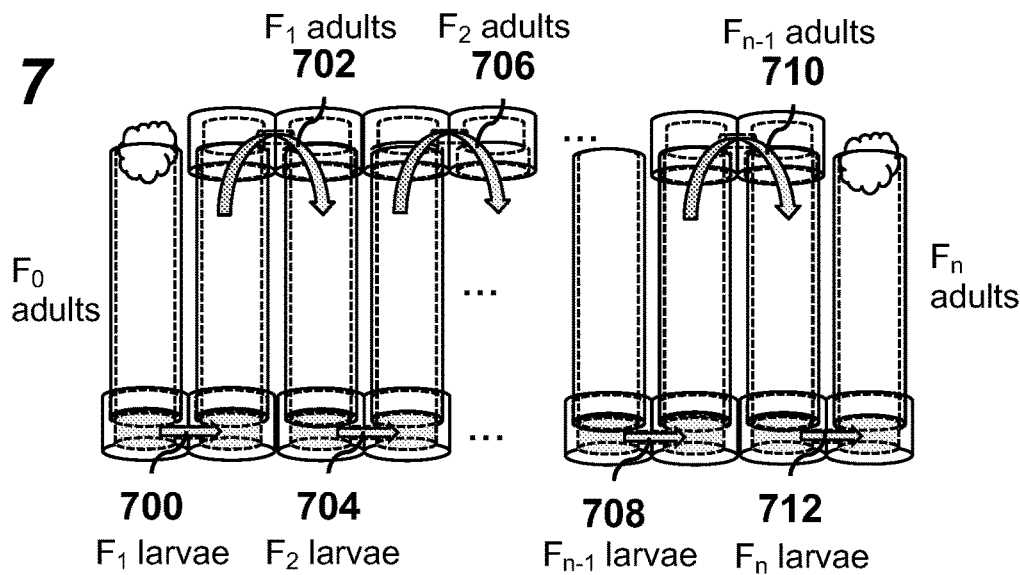

$F_1$ adults 702, $F_2$ adults 706, $F_{n-1}$ adults 710

$F_0$ adults, $F_n$ adults

700 $F_1$ larvae, 704 $F_2$ larvae, 708 $F_{n-1}$ larvae, 712 $F_n$ larvae

*Fig. 8*
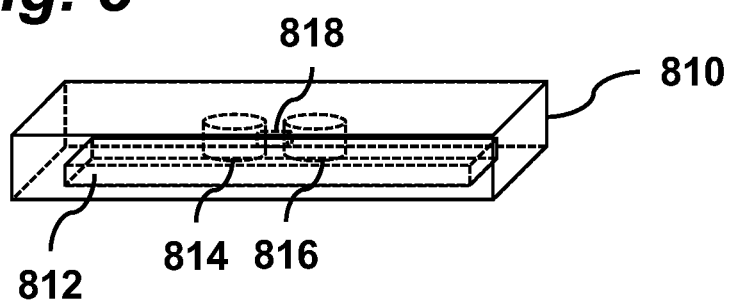
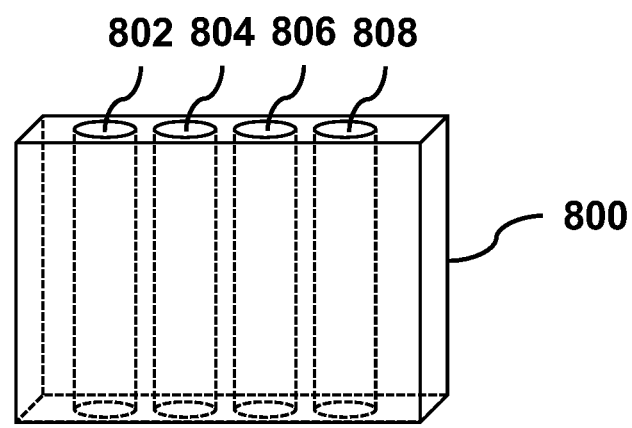
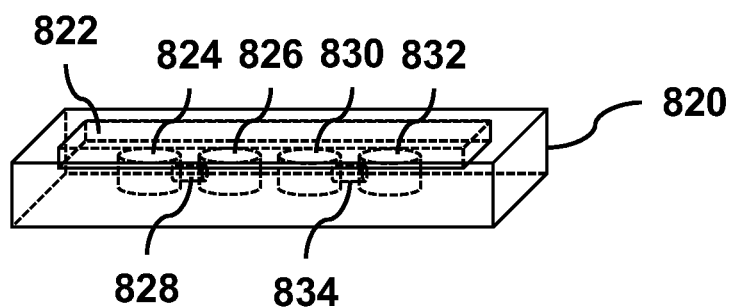

_DROSOPHILA_ STOCK MAINTENANCE

CROSS REFERENCE TO RELATED APPLICATIONS

The present application is a divisional application of U.S. patent application Ser. No. 17/585,338, filed on Jan. 26, 2022, which is a divisional of U.S. patent application Ser. No. 16/159,596 filed on Oct. 12, 2018, which claims the benefit of and priority to U.S. Provisional Patent Application No. 62/577,457 filed on Oct. 26, 2017. The entire disclosures of the foregoing applications are incorporated by reference herein.

FIELD OF THE INVENTION

The present invention relates generally to techniques for maintaining cultures of insects. More specifically, it relates to methods and systems for maintenance of _Drosophila melanogaster_ and other insects.

BACKGROUND OF THE INVENTION

_Drosophila melanogaster_ is a species of fly that is widely used in laboratories for genetics research and instruction. Its life cycle includes an egg, larva, pupa and flying adult. In the laboratory, live cultures of flies are commonly maintained in containers with a food media in the bottom. Adults lay eggs on the food media, and when the eggs hatch, the larvae and pupae feed on the food media. After they mature into adults flies, the adults are transferred to a new container with fresh food media. The transfer is a manual task performed by a laboratory technician. To help prevent the escape of flying adults during transfer, and to allow examination and sorting, they are often immobilized for transfer by chilling or anesthetizing them.

To maintain a healthy culture, the flies should be transferred to a new container every 10 to 14 days. Worldwide it is estimated between 600,000-700,000 stocks must be transferred manually twice a month. Although there are robotic systems available for this task, these systems are expensive and not practical for small laboratories or instructional purposes. There is thus a long-standing need for an inexpensive and less labor-intensive method and system for maintaining cultures of _Drosophila melanogaster_ in the laboratory.

BRIEF SUMMARY OF THE INVENTION

The present invention provides a method and system for maintenance of _Drosophila melanogaster_ cultures that is simple, inexpensive, and far less labor intensive than existing methods. It takes advantage of fundamental differences in behavior and locomotion between the larva and adult insect stages, and a unique system of connecting a sequence of containers. The need for a technician to transfer each new generation by hand is eliminated, allowing healthy stocks to be maintained automatically for months. Another advantage is that the system automatically separates distinct generations of fruit flies from each other. In addition, because the stocks are constantly maintained in a linear array of vials, it eliminates the potential for contamination and mis-labeling, a well known issue in stock maintenance.

In one aspect, the invention provides a method for maintaining insect cultures using four (or more) open-ended cylindrical tubes (e.g., a first tube, second tube, third tube, and fourth tube) and three (or more) dual-cap connectors (e.g., a first dual cap, a second dual cap, and a third dual cap). Each of the dual-capped connectors has an opening from an inside of its first cap to an inside of its second cap. The open-ended cylindrical tubes are connected in sequence using the dual-capped connectors, by connecting the bottom of the first tube to the bottom of the second tube using the first dual cap which is filled with food media, connecting the top of the second tube to the top of the third tube using the second dual cap, and connecting the bottom of the third tube to the bottom of the fourth tube using the third dual cap which is filled with food media. Thus, the tubes are arranged in a sequence with alternating passageways: the bottom dual caps are filled with food media so that only larvae can pass from one tube to the other, and the top dual caps have unfilled openings so that only flying adults can pass from one tube to the other. Insects are inserted into the first tube, which is then capped with a terminal cap lacking an opening such as a cotton ball or single (as opposed to dual) cap that caps a single tube and lacks an opening. The flies lay eggs in the food media at the bottom. These eggs grow into first generation larvae that eat the food media and propagate through the first dual cap from the first tube to the second tube. These first generation larvae then mature into first generation adults in the second tube. Since they can fly, these first generation adults propagate through the second dual cap from the top of the second tube to the top of the third tube where they lay eggs in the food media at the bottom of the third tube. These eggs grow into second generation larvae that propagate through the third dual cap from the third tube to the fourth tube where they mature into second generation adults in the fourth tube. The process can continue with additional tubes.

In another aspect, the invention provides an insect culture maintenance kit including four or more open-ended cylindrical tubes (a first tube, second tube, third tube, and fourth tube), three or more dual-cap connectors (a first dual cap, a second dual cap, and a third dual cap), and (optionally) one or more terminal caps. Each of the three dual-capped connectors has an opening from an inside of a first cap to an inside of a second cap. The open-ended cylindrical tubes and the dual-capped connectors are sized such that the caps of the dual-capped connectors fit on the ends of the four open-ended cylindrical tubes to close the ends, allowing the open-ended cylindrical tubes to be connected in sequence using the dual-capped connectors. Optionally, the dual-cap connectors may be of two different types, where a first type has a first opening size providing a passageway between the caps, and a second type has a second opening size providing a passageway between the caps, where the first opening size is different from the second opening size.

In another aspect, the invention provides a dual-capped connector comprising a first cap having a first cylindrical inner cap wall defining a first cylindrical region within an inside of the first cap; a second cap having a second cylindrical inner cap wall defining a second cylindrical region within an inside of the second cap; a reinforcing portion that mechanically connects the first cap with the second cap; and a channel forming a passageway from the inside of the first cap to the inside of the second cap to form a single connected space. The dual capped connector preferably is made of a single molded ductile material such as plastic, silicone or rubber.

In some implementations, the first cap further comprises a first cylindrical space within the inside of the first cap, wherein the first cylindrical space has a first inner diameter smaller than a first diameter of the first cylindrical inner cap wall; and the second cap further comprises a second cylindrical space within the inside of the second cap, wherein the second cylindrical space has a second inner diameter smaller than a second diameter of the second cylindrical inner cap wall. The channel forms a passageway from the inside of the first cap to the inside of the second cap connects the first cylindrical space to the second cylindrical space.

BRIEF DESCRIPTION OF THE SEVERAL VIEWS OF THE DRAWINGS

FIG. 1 is a perspective view of a collection of tubes and dual-cap connectors that may be assembled to form an insect culture maintenance system, according to an embodiment of the invention.

FIG. 2A and FIG. 2B are a top view and perspective view, respectively, of a dual-cap connector, according to an embodiment of the invention.

FIG. 6 is a flowchart outlining the steps of a method for maintaining an insect culture, according to an embodiment of the invention.

FIG. 7 is a perspective view of an assembled insect culture maintenance system illustrating the movement of insects through the system, according to an embodiment of the invention.

FIG. 8 is a perspective view of components of an insect culture maintenance system, according to an embodiment of the invention.

DETAILED DESCRIPTION OF THE INVENTION

Figure 3:
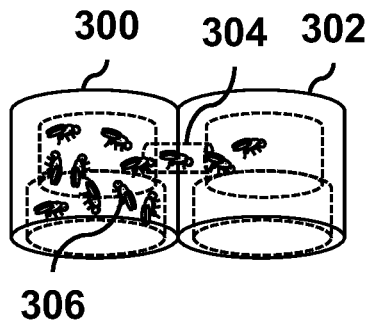
FIG. 3 is a perspective view of a dual-cap connector, illustrating the movement of flies from the inside of one cap to the inside of another, according to an embodiment of the invention.

In one embodiment of the present invention, an insect culture system may be assembled from a collection of components, which may be provided in the form of a kit. For example, FIG. 1 shows a collection of tubes 100a, 100b, 100c, 100d and dual-cap connectors 102a, 102b, 102c that may be assembled to form an insect culture maintenance system. The tubes and the dual-capped connectors are sized such that the caps of the dual-capped connectors fit on the ends of the tubes to close the ends. The tubes are open-ended cylindrical tubes preferably made of a durable, rigid, transparent material such as glass or hard plastic. Although the tubes are preferably open-ended cylinders, they could also have one or both ends be partially closed, or closed with a small hole, e.g., 3/16 inch (5 mm) or more in diameter.

Two detailed views of a dual-capped connector are shown in FIG. 2A and FIG. 2B. The dual-cap connector is preferably made of a single molded material, preferably a durable material such as plastic, silicone or rubber which may be partly ductile to facilitate placement of the caps on the ends of the tubes. Reinforcing portion 114 provides mechanical strength to help ensure that the two caps of the dual-capped connector do not break apart.

The connector has two caps, each designed to cover an end of one of the tubes. Specifically, the two cylindrical regions 116 and 118 are designed so that the ends of two tubes may be securely inserted into them. For example, the outer surface of one tube forms a fit with the cylindrical inner cap wall 104. The caps include cylindrical spaces 110 and 112 that remain above the lip of an inserted tube. For example, the cylindrical inner cap wall 106 has a diameter smaller than the outer diameter of the inserted tube, e.g., it may be equal to the inner diameter of the inserted tube. An essential feature of the dual-capped connector is the opening 108 connecting the cylindrical spaces 110 and 112 to form a single connected space. The channel 108 is preferably oriented horizontally and positioned within the inside of the caps at a vertical position such that it is not close to the rim of an inserted tube. This passageway or channel 108 from the inside of the first cap to the inside of the second cap preferably has a 3/16 inch (5 mm) diameter cylindrical shape. In some embodiments, there may be different channel diameters for different dual-cap connectors. For example, the dual-cap connectors may be of two different types, where first and second types have different opening sizes. The dual-cap connector shown in these figures is illustrative, and those skilled in the art will appreciate that various other designs can implement the same function. For example, in alternative embodiments, the dual-cap connector is formed of two separate caps with holes connected by a short tube. Yet another embodiment is discussed below in relation to FIG. 8.

Figure 5:
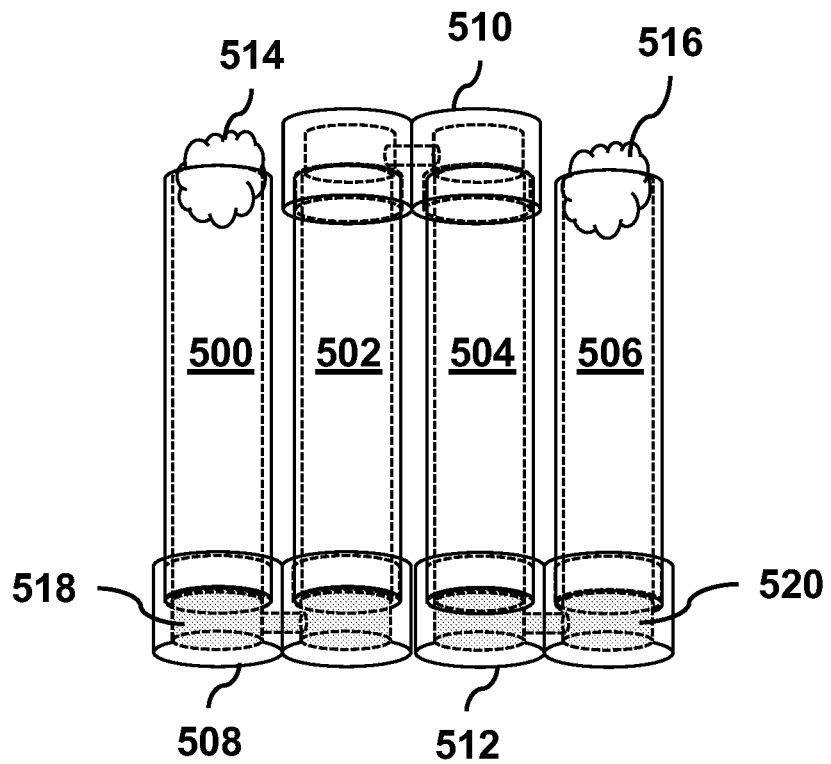
FIG. 5 is a perspective view of an assembled insect culture maintenance system, according to an embodiment of the invention.

FIG. 5 illustrates how the tubes and dual-cap connectors are assembled to form an insect culture maintenance system. Four cylindrical tubes 500, 502, 504, 506 are arranged with their longitudinal axes in parallel. The axes do not necessarily need to be in the same plane. First and second tubes 500 and 502 are connected at their bottoms with a dual-cap connector 508. Similarly, third and fourth tubes 504 and 506 are connected at their bottoms with a dual-cap connector 512. Second and third tubes 502 and 504 are connected at their tops with a dual cap connector 510, which may be of a different type than connectors 508 and 512. The tops of the first tube 500 and fourth tube 506 are capped or plugged, e.g., with terminal caps 514 and 516 (shown as cotton balls in FIG. 5).

Figure 4:
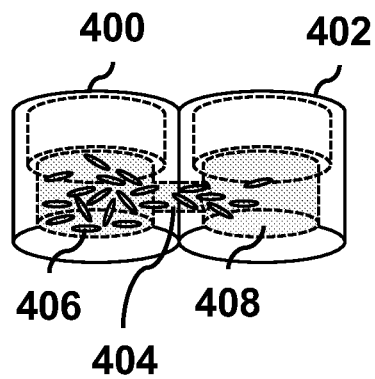
FIG. 4 is a perspective view of a dual-cap connector, illustrating the movement of larvae from the inside of one cap to the inside of another, according to an embodiment of the invention.

Connectors 508 and 512 are half-filled with food media 518 and 520, respectively. As illustrated in FIG. 4, as larvae 406 eat the food media 408, they can move through channel 404 from the inside of cap 400 to the inside of cap 402, according to an embodiment of the invention. In contrast, the movement of adult insects from the inside of cap 400 to the inside of cap 402 is blocked by the food media 408. The food media fills only the deepest inside half of the cap (e.g., space 110 of FIG. 2B), leaving the other half (e.g., space 116 of FIG. 2B) clear for unobstructed insertion of the tube. In alternative embodiments, the food media can completely fill the entire cap. This can be achieved, for example, by filling the cap with food media after insertion of the tube into the cap.

Returning to FIG. 5, connector 510 is not filled with food media, so that its open passageway allows adult (flying or crawling) insects to freely pass from tube 502 to tube 504. The length of the tubes is such that the larva are unlikely to crawl to the top of the tube. The tube can be provided in any such length including at least 60 mm, at least 70 mm, at least 80 mm, at least 90 mm, at least 95 mm, at least 100 mm, at least 110 mm, at least 120 mm at least 150 mm, or more than 150 mm in length, or can be provided in any range of length such as between 60 mm and 150 mm, between 90 mm and 110 mm, or between 93 mm and 97 mm. As illustrated in FIG. 3, flies 306 can move freely through channel 304 from the inside of cap 300 to the inside of cap 302. In contrast, the eggs, larvae, and pupae are confined to the bottom of the tube where the food media is located. Thus, the tubes in FIG. 5 are arranged in a sequence with alternating passageways: the bottom dual caps are filled with food media so that only larvae can pass from one tube to the other, and the top dual caps have unfilled openings so that only flying adults can pass from one tube to the other.

The steps of a method for maintaining an insect culture using the system described above is shown in the flowchart of FIG. 6. These steps will be described with reference to the assembled insect culture maintenance system shown in FIG. 7. In step 600, a sequence of tubes are connected using dual-cap connectors, where the connectors at the bottoms of the tubes are filled with food media, while the connectors at the tops of the tubes are not filled with food media. $F_0$ adult insects are inserted in the first tube, and the tube is capped to prevent their escape. The $F_0$ adults lay $F_1$ generation eggs in the food media. In step 602, these $F_1$ eggs grow into $F_1$ generation larvae 700 that eat the food media and propagate through the first dual cap from the first tube to the second tube. These $F_1$ generation larvae then mature into $F_1$ generation adults 702 in the second tube. In step 604, these $F_1$ generation adults 702 propagate through the second dual cap from the top of the second tube to the top of the third tube where they lay $F_2$ generation eggs in the food media at the bottom of the third tube. In step 606, these $F_2$ eggs grow into $F_2$ generation larvae 704 that propagate through the third dual cap from the third tube to the fourth tube where they mature into $F_2$ generation adults 706 in the fourth tube. Steps analogous to steps 604 and 606 can be repeated for subsequent generations with additional tubes and connectors. As shown in the figure, $F_{n-1}$ larvae 708 mature into $F_{n-1}$ generation adults 710 which propagate via a top connector to the next tube. The $F_{n-1}$ generation adults 710 then lay $F_n$ generation eggs that mature into $F_n$ generation larvae 712 which propagate via a bottom connector to the next tube. The process concludes as the $F_n$ generation larvae 712 mature into $F_n$ generation adults in the last tube.

As shown in FIG. 8, in an alternate embodiment of an insect culture maintenance system, the sequence of tubes 802, 804, 806, 808 has the form of a single slab 800 of material with parallel cylindrical passageways through it, and the sequence of caps has the form of a first multi-cap connector 810 to cover the tops of the cylindrical passageways 802, 804, 806, 808, and a second multi-cap connector 820 to cover the bottoms of the cylindrical passageways 802, 804, 806, 808. The multi-cap connectors have one or more dual-cap connectors built in to them to provide the same functionality as separate dual-cap connectors. The top multi-cap connector 810 has a space 812 cut out so that it fits over the top end of slab 800. Similarly, the bottom multi-cap connector 820 has a space 822 cut out so that it fits over the top end of slab 800. The top multi-cap connector 810 includes a single dual-cap connector with caps 814 and 816 joined by channel 818. The bottom multi-cap connector 820 includes two dual-cap connectors, one with caps 824 and 826 joined by channel 828, and another with caps 830 and 832 joined by channel 834.

The invention claimed is:

1. An insect culture system comprising:
a first cap having a top wall and a cylindrical side wall extending from the top wall, the top wall and the cylindrical side wall of the first cap defining a first cavity configured to receive an open end of a first tube, the cylindrical side wall of the first cap having a first side opening;
a second cap having a top wall and a cylindrical side wall extending from the top wall, the cylindrical side wall of the second cap defining a second cavity configured to receive an open end of a second tube, the cylindrical side wall of the second cap having a second side opening; and
a channel interconnecting the first side opening and the second side opening for propagating insects between a first tube coupled to the first cap and a second tube coupled to the second cap.

2. The insect culture system according to claim 1, wherein the cylindrical side wall of the first cap has a first inner diameter defining a first cylindrical region and a second inner diameter defining a first cylindrical space, wherein the second inner diameter is smaller than the first inner diameter such that the first tube is insertable only into the first cylindrical region.

3. The insect culture system according to claim 2, wherein the first cylindrical region is concentric with the first cylindrical space.

4. The insect culture system according to claim 1, wherein the cylindrical side wall of the second cap has a second inner diameter defining a second cylindrical region and a second inner diameter defining a second cylindrical space, the second inner diameter is smaller than the second inner diameter such that the second tube is insertable only into the second cylindrical region.

5. The insect culture system according to claim 4, wherein the second cylindrical region is concentric with the second cylindrical space.

6. The insect culture system according to claim 1, wherein the first cap, the second cap, and the channel are a unitary structure made of a single molded ductile material.

7. The insect culture system according to claim 1, wherein each of the first cap, the second cap, and the channel is made of at least one of plastic, silicone, or rubber.

8. An insect culture system comprising:
a first tube having a first open end;
a second tube having a second open end; and
a dual-capped connector including:
a first cap including a top wall and a cylindrical side wall extending from the top wall, the top wall and the cylindrical side wall of the first cap defining a first cavity configured to receive the first open end of the first tube, the cylindrical side wall of the first cap having a first side opening;
a second cap including a top wall and a cylindrical side wall extending from the top wall, the cylindrical side wall of the second cap defining a second cavity configured to receive the second open end of the second tube, the cylindrical side wall of the second cap having a second side opening; and
a channel interconnecting the first side opening and the second side opening for propagating insects between the first tube and the second tube.

9. The insect culture system according to claim 8, wherein the cylindrical side wall of the first cap has a first inner diameter defining a first cylindrical region and a second inner diameter defining a first cylindrical space, wherein the second inner diameter is smaller than the first inner diameter such that the first tube is insertable only into the first cylindrical region.

10. The insect culture system according to claim 9, wherein the first cylindrical region is concentric with the first cylindrical space.

11. The insect culture system according to claim 8, wherein the cylindrical side wall of the second cap has a second inner diameter defining a second cylindrical region and a second inner diameter defining a second cylindrical space, wherein the second inner diameter is smaller than the second inner diameter such that the second tube is only insertable only into the second cylindrical region.

12. The insect culture system according to claim 11, wherein the second cylindrical region is concentric with the second cylindrical space.

13. The insect culture system according to claim 8, wherein the dual-capped connector is made of a single molded ductile material.

14. The insect culture system according to claim 8, wherein the dual-capped connector is made of at least one of plastic, silicone, or rubber.

\* \* \* \* \*